Figure 1A:
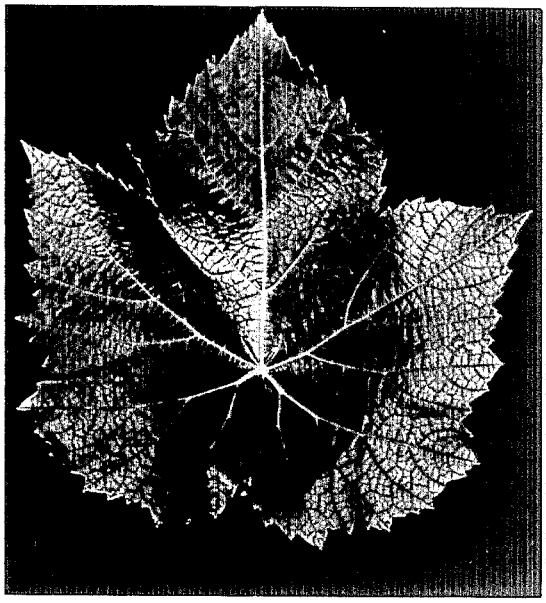

United States Patent [19]

Reisch et al.

[11] Patent Number: Plant 6,160

[45] Date of Patent: Apr. 26, 1988

[54] GRAPEVINE, EINSET SEEDLESS

[75] Inventors: Bruce I. Reisch; Robert M. Pool, both of Geneva; John P. Watson, Phelps; George W. Remaily, Hammondsport, all of N.Y.; John Einset, deceased, late of Geneva, N.Y., by Hjordis Einset, executrix

[73] Assignee: Cornell Research Foundation, Inc., Ithaca, N.Y.

[21] Appl. No.: 795,573

[22] Filed: Nov. 5, 1985

[51] Int. Cl.[4] ..... A01H 5/03
[52] U.S. Cl. ..... Plt./47
[58] Field of Search ..... Plt./47

[56] References Cited

PUBLICATIONS

Proceedings of the 17th Pennsylvania Grape Industry Conference, Feb. 27 and 28, 1985 entitled "Potential Table Grape Varieties".

Rochester Democrat and Chronicle, Sep. 20, 1985, Nov. 10, 1985.

Eastern Grape Growers and Winery News, Apr./May 1985, pp. 21–25.

*Primary Examiner*—Robert E. Bagwill
*Attorney, Agent, or Firm*—Jones, Tullar & Cooper

[57] ABSTRACT

A new and distinct variety of grapevine from an interspecific cross (*Labruscana*×*vinifera*), named 'Einset Seedless' and tested as NY 63.878.1 which originated from a seed produced by hand pollination of 'Fredonia' (non-patented) with pollen from 'Canner' (non-patented) is described. This new grapevine variety can be distinguished by its early maturing seedless fruit of attractive red color, having a unique mild American flavor, firm texture and adherent skin. Winter hardiness is good and storage life is considered to be excellent.

2 Drawing Sheets

SUMMARY

This invention is a new and distinct variety of grapevine from our interspecific cross (*Labruscana*×*vinifera*) which can be distinguished by its early maturing seedless fruit of attractive red color, having a unique mild American flavor, firm texture and adherent skin. Winter hardiness is good and storage life is considered to be excellent.

ORIGIN

'Einset Seedless' was developed by a breeding program of the Department of Horticultural Sciences, Cornell University, New York State Agricultural Experiment Station, Geneva, N.Y. 'Einset Seedless' originated from a seed produced by hand-pollination of 'Fredonia' with the pollen from 'Canner'. The cross of 'Fredonia'×'Canner' ('Hunisa'×'Sultanina') was made in 1963 by G. W. Remaily. It was tested as NY 63.878.1. The original seedling was planted in 1965 and fruited in 1967. Own-rooted vines were propagated for further testing and were first planted in 1969.

DESCRIPTION

The berries of 'Einset Seedless' are ovoid and bright red in color with a light waxy bloom. The flowers are perfect. The medium soft seed remnant is not usually noticeable. Berries are medium size in the absence of gibberellin treatment or girdling. The skin is slightly tough, adherent and resistant to cracking. The flesh is tender to firm and the flavor is fruity with a mild note of labrusca and strawberry character. The grapes are pleasantly sweet with a high brix/acid ratio. The shouldered clusters are medium-small in size and attractive.

In preliminary tests, the fruit responds very well to gibberellin sprays, and when used precautions should be taken to avoid overcropping. In such cases cluster thinning may be required. Clusters are loose to well-filled and therefore have room for GA-increased berry size.

In storage tests with in-packge $SO_2$ generators, the fruit were rated marketable in late November and late December in 1983. When stored in cardboard masters (at lower $SO_2$ levels) in 1984, the fruit were rated marketable in late November and unacceptable in late December.

Own-rooted vines are vigorous and moderately productive when grown in phylloxera (*Daktulosphaira vitifoliae* Fitch)-infested soils. The vines are susceptible to powdery mildew (*Uncinula necator* [Schw.] Burr.) and resistant to botrytis bunch rot (*Botrytis cinerea* Pers.). A spray schedule which is more rigorous than necessary to control powdery mildew on 'Concord' has been required for 'Einset Seedless' in New York. Downy mildew (*Plasmopara viticola* [Berk. and Curt.] Berl. & de Toni) has appeared on the fruit clusters in some years. Its resistance to black rot (*Guignardia bidwelli* [Ell.] Viala and Ravaz) is unknown since black rot has not been troublesome at Geneva.

Trunk injury due to cold has been very rare. The original seedling, planted in 1965, was injured in 1968 and 1970. No other trunk injury has been recorded in any Geneva planting. Crown gall (*Agrobacterium tumefaciens* [E. F. Sm. & Towns.] Conn.) has not been observed. Winter hardiness of buds ranks with the best of the seedless table grapes. Following the severe winter of 1980–81, 'Canadice', 'Remaily Seedless' and 'Einset Seedless' had 70, 93, and 65% shootless nodes. At a nearby but slightly better site, 'Concord', 'Himrod', and 'Lakemont' had 6, 56 and 80% shootless nodes, respectively. At the Vineyard Laboratory (Fredonia, N.Y.), 'Einset Seedless', 'Himrod', 'Lakemont', and 'Remaily Seedless' had 32, 42, 67 and 83% shootless nodes, respectively, in 1984.

The new cultivar has been named 'Einset Seedless', for Dr. John Einset, one of the outstanding fruit cytogeneticists and fruit breeders of the world. Dr. Einset, now deceased, was a staff member of the New York State Agricultural Experiment Station from 1942 to 1973 including an 18 year period as head of the Department of Pomology. His contributions, inspiration and outstanding abilities were recognized by all associated with him, and his impact upon the direction of the grape breeding program will be a lasting one.

DESCRIPTION OF PHOTOGRAPHS

The accompanying photographs show typical specimens of the fruit and leaves of the new variety in color as nearly true as it is reasonably possible to make in a color illustration of this character.

Figure 1B:
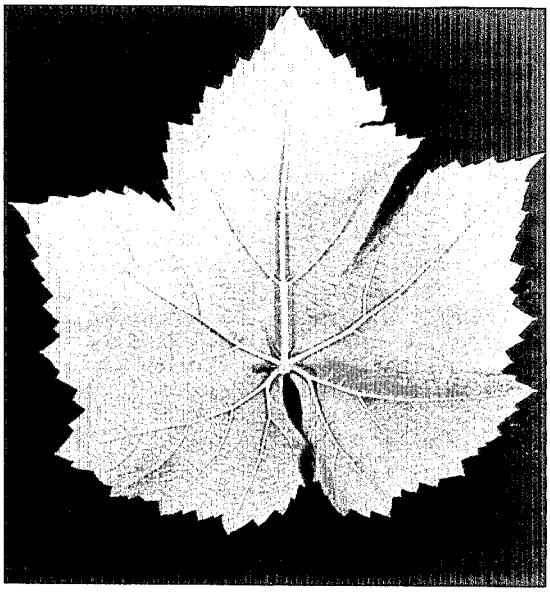
Figure 1C:
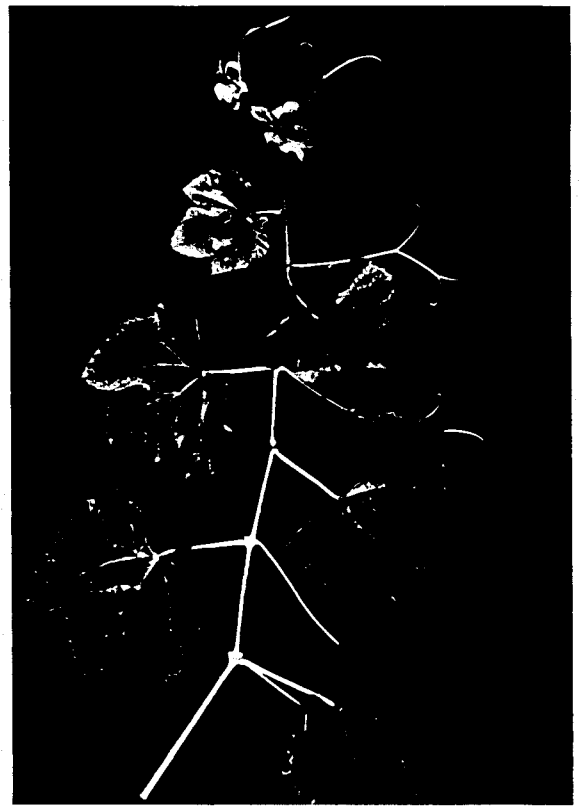
Figure 1D:
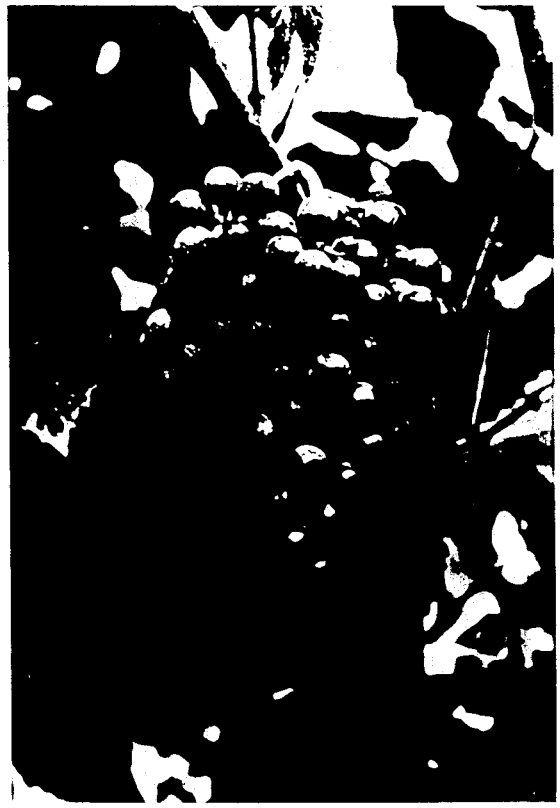

FIG. 1. A-Mature leaf, upper surface, B-mature leaf, lower surface, C-young shoot and D-fruit cluster of 'Einset Seedless'.

The following is a detailed description of the pomological characteristics of the subject grapevine. Color terminology is in accordance with that of "The Royal Horticultural Society Colour Chart" published in 1966 by The Royal Horticultural Society of London, England.

Where dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected.

The descriptions reported herein are from specimens grown at Geneva, N.Y.

Vines: Medium vigor, ca. 1.0 kg cane prunings/vine/-year, semi-upright to horizontal growth. Bud break comes shortly after Concord. The trunk is strong and sheds bark in short, longitudinal strips. Bark color is grey group 201D on a greyed purple 187A (approximate) background.

Shoot tip: Curved to form a 60° to 90° angle, with wooly downy indument. The tip is open, not globular having a white color with rose margins.

Shoot: Inflorescences are usually borne on nodes 4 and 5, occasionally nodes 3 and 4 from the base; lateral shoot production is low. Tendrils are wiry, slender with one or two branch points occurring in a discontinuous arrangement along the shoot length, averaging 16.7 cm.

Mature leaves: 5-lobed, cordiform shape with a deep, narrow, slightly open to closed petiolar sinus and deep overlapping, closed superior sinus. Upper surface is glabrous, flat, bullate and green 137A in color. Lower surface with sparse, wooly hairs, green 146B-C in color.

Flowering: Approximately one week after 'Concord'.

Clusters: Medium-small without gibberellin treatment, averaging 135 g per cluster. Clusters are shouldered and tapering, usually borne 2 per shoot on primary shoots, very rarely occurring on secondary, tertiary and lateral shoots. Clusters are loose to moderately well-filled without gibberellin treatment.

Fruit: Ovoid, medium-sized (ca. 2.3 g/berry), with slightly tough, adherent, crack resistant skin, and firm to tender flesh having an outstanding mild American, sometimes strawberry, flavor. Berries are seedless with rudimentary medium-sized soft seeds, not usually noticeable. There is a light waxy bloom. Berry color is red-purple 59B-C.

Fruit analysis: Three-year average 19.9° Brix, 7.2 g/l acid, Brix/acid ratio of 27.9.

Keeping quality: Excellent in refrigerated storage with good flavor and color retention, especially with $SO_2$ in-package generators.

| | Isozyme analysis: Phosphoglucose isomerase (GPI) Rf | | | | | | |
|---|---|---|---|---|---|---|---|
| | 0.09 | 0.23 | 0.26 | 0.28 | 0.33 | 0.36 | 0.56 |
| Einset Seedless | | | | + | + | + | + |
| Reliance | | + | | + | | + | + |
| Challenger | | + | | + | | + | + |
| Canadice | | + | | + | | + | + |
| Suffolk Red | | + | + | + | | | + |
| Vanessa | | + | | + | | + | + |
| Fredonia | | + | + | + | | | + |
| Concord | + | | | | | | + |

We claim:

1. The new and distinct variety of grapevine herein described and illustrated and identified by the characteristics enumerated above.

* * * * *